United States Patent
Moffitt et al.

(10) Patent No.: US 9,901,737 B2
(45) Date of Patent: Feb. 27, 2018

(54) SYSTEMS AND METHODS FOR PROVIDING THERAPY TO A PATIENT USING INTERMITTENT ELECTRICAL STIMULATION

(71) Applicant: Boston Scientific Neuromodulation Corporation, Valencia, CA (US)

(72) Inventors: Michael A. Moffitt, Valencia, CA (US); Stephen Carcieri, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/861,471

(22) Filed: Sep. 22, 2015

(65) Prior Publication Data

US 2016/0082254 A1 Mar. 24, 2016

Related U.S. Application Data

(60) Provisional application No. 62/053,509, filed on Sep. 22, 2014.

(51) Int. Cl.
 *A61N 1/00* (2006.01)
 *A61N 1/36* (2006.01)
 *A61N 1/378* (2006.01)

(52) U.S. Cl.
 CPC .......... *A61N 1/36071* (2013.01); *A61N 1/36* (2013.01); *A61N 1/36139* (2013.01);
 (Continued)

(58) Field of Classification Search
 CPC .............................. A61N 1/36071; A61N 1/36
 (Continued)

(56) References Cited

U.S. PATENT DOCUMENTS

| 4,813,418 A | 3/1989 | Harris |
| 6,067,474 A | 5/2000 | Schulman et al. |

(Continued)

FOREIGN PATENT DOCUMENTS

| DE | 10318071 A1 | 11/2004 |
| WO | 02/09808 A1 | 2/2002 |
| WO | 2009/055127 A1 | 4/2009 |

OTHER PUBLICATIONS

Larson, J. et al., "Reversal of LTP by theta frequency stimulation", Brain Research, Elsevier, Amsterdam, NL, vol. 600 No. 1, Jan. 8, 1993, pp. 97-102.

(Continued)

*Primary Examiner* — Nadia A Mahmood
(74) *Attorney, Agent, or Firm* — Lowe Graham Jones PLLC; Bruce E. Black

(57) ABSTRACT

A method for providing therapy to a patient using intermittent electrical stimulation includes advancing a plurality of electrodes disposed along a distal portion of a lead to a target stimulation location within a patient. A proximal portion of the lead is coupled to an electrical stimulator disposed external to the patient. Patient tissue at the target stimulation location is stimulated for a first duration of time that is no greater than one day using the plurality of electrodes. The stimulation provides efficacious treatment to the patient for a second duration of time that is at least twice as long as the first duration of time. Stimulation is ceased after completion of the first duration of time. The lead is removed from the patient after ceasing stimulation and prior to an end of the second duration of time.

19 Claims, 11 Drawing Sheets

(52) U.S. Cl.
CPC ............ *A61N 1/378* (2013.01); *A61N 1/3605* (2013.01); *A61N 1/3787* (2013.01)

(58) Field of Classification Search
USPC .................................................... 607/46, 57
See application file for complete search history.

(56) References Cited

U.S. PATENT DOCUMENTS

| | | | |
|---|---|---|---|
| 6,181,969 B1 | 1/2001 | Gord | |
| 6,516,227 B1 * | 2/2003 | Meadows | ............ A61N 1/0553 607/117 |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,244,150 B1 | 7/2007 | Brase et al. | |
| 7,437,193 B2 | 10/2008 | Parramon et al. | |
| 7,450,997 B1 | 11/2008 | Pianca et al. | |
| 7,672,734 B2 | 3/2010 | Anderson et al. | |
| 7,761,165 B1 | 7/2010 | He et al. | |
| 7,783,359 B2 | 8/2010 | Meadows | |
| 7,792,590 B1 | 9/2010 | Pianca et al. | |
| 7,809,446 B2 | 10/2010 | Meadows | |
| 7,917,221 B2 | 3/2011 | Tass | |
| 7,949,395 B2 | 5/2011 | Kuzma | |
| 7,974,698 B2 | 7/2011 | Tass et al. | |
| 7,974,706 B2 | 7/2011 | Moffitt et al. | |
| 8,000,794 B2 | 8/2011 | Lozano | |
| 8,000,795 B2 | 8/2011 | Lozano | |
| 8,000,796 B2 | 8/2011 | Tass et al. | |
| 8,078,275 B2 | 12/2011 | Lozano | |
| 8,116,874 B2 | 2/2012 | Tass | |
| 8,175,710 B2 | 5/2012 | He | |
| 8,224,450 B2 | 7/2012 | Brase | |
| 8,271,094 B1 | 9/2012 | Moffitt et al. | |
| 8,280,514 B2 | 10/2012 | Lozano et al. | |
| 8,295,944 B2 | 10/2012 | Howard et al. | |
| 8,346,365 B2 | 1/2013 | Lozano | |
| 8,364,278 B2 | 1/2013 | Pianca et al. | |
| 8,380,304 B2 | 2/2013 | Lozano | |
| 8,391,985 B2 | 3/2013 | McDonald | |
| 8,463,378 B2 | 6/2013 | Tass | |
| 8,463,386 B2 | 6/2013 | Tass | |
| 8,538,547 B2 | 9/2013 | Tass et al. | |
| 8,565,883 B2 | 10/2013 | Lozano | |
| 8,612,006 B2 | 12/2013 | Lozano et al. | |
| 8,868,191 B2 | 10/2014 | Lozano | |
| 9,227,066 B2 | 1/2016 | Lozano | |
| 2003/0191506 A1 | 10/2003 | Shloznikov | |
| 2004/0210271 A1 | 10/2004 | Campen | |
| 2005/0075696 A1 | 4/2005 | Forsberg et al. | |
| 2005/0216071 A1 | 9/2005 | Devlin et al. | |
| 2006/0015153 A1 | 1/2006 | Bradford et al. | |
| 2006/0212090 A1 | 9/2006 | Lozano et al. | |
| 2007/0142874 A1 | 6/2007 | John | |
| 2007/0150036 A1 | 6/2007 | Anderson | |
| 2007/0225674 A1 | 9/2007 | Molnar et al. | |
| 2008/0071325 A1 | 3/2008 | Bradley | |
| 2008/0215113 A1 | 9/2008 | Pawlowicz | |
| 2009/0082829 A1 | 3/2009 | Panken et al. | |
| 2009/0112281 A1 | 4/2009 | Miyazawa et al. | |
| 2009/0187222 A1 | 7/2009 | Barker | |
| 2009/0276021 A1 | 11/2009 | Meadows et al. | |
| 2010/0268298 A1 | 3/2010 | Pianca et al. | |
| 2010/0076535 A1 | 5/2010 | Pianca et al. | |
| 2011/0004267 A1 | 1/2011 | Meadows et al. | |
| 2011/0077720 A1 | 3/2011 | Torgerson et al. | |
| 2011/0078900 A1 | 4/2011 | Pianca et al. | |
| 2011/0130817 A1 | 6/2011 | Chen | |
| 2011/0130818 A1 | 6/2011 | Chen | |
| 2011/0201977 A1 | 8/2011 | Tass | |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | Digiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 | 8/2012 | DiGiore et al. | |
| 2012/0203321 A1 | 8/2012 | Moffitt et al. | |
| 2012/0274273 A1 | 11/2012 | Jacobs et al. | |
| 2012/0316615 A1 | 12/2012 | DiGiore et al. | |
| 2013/0105071 A1 | 5/2013 | DiGiore et al. | |
| 2013/0218239 A1 | 8/2013 | Grill et al. | |
| 2013/0231713 A1 | 9/2013 | De Ridder | |
| 2013/0289385 A1 | 10/2013 | Lozano et al. | |
| 2013/0317583 A1 | 11/2013 | Pianca | |
| 2013/0317585 A1 | 11/2013 | Barker | |
| 2013/0317586 A1 | 11/2013 | Pianca | |
| 2013/0317587 A1 | 11/2013 | Barker | |
| 2013/0317588 A1 | 11/2013 | Howard et al. | |
| 2014/0025133 A1 | 1/2014 | Lozano | |
| 2014/0081349 A1 | 3/2014 | Lee et al. | |
| 2014/0277281 A1 | 9/2014 | Grandhe | |
| 2016/0030666 A1 | 2/2016 | Lozano et al. | |

OTHER PUBLICATIONS

International Search Report and Written Opinion for Application PCT/US2015/051445 dated Dec. 15, 2015, 16 pages.

* cited by examiner

… (1)

SYSTEMS AND METHODS FOR PROVIDING THERAPY TO A PATIENT USING INTERMITTENT ELECTRICAL STIMULATION

CROSS-REFERENCE TO RELATED APPLICATIONS

This application claims the benefit under 35 U.S.C. § 119(e) of U.S. Provisional Patent Application Ser. No. 62/053,509, filed Sep. 22, 2014, which is incorporated herein by reference.

FIELD

The present invention is directed to the area of electrical stimulation systems and methods of using the systems. The present invention is also directed to systems and methods for providing therapy to a patient using intermittent electrical stimulation generated from an electrical stimulation system.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include an implantable pulse generator (IPG), one or more leads, and an array of stimulator electrodes on each lead. The stimulator electrodes are in contact with or near the nerves, muscles, or other tissue to be stimulated. The pulse generator generates electrical pulses that are delivered by the electrodes to body tissue.

BRIEF SUMMARY

In one embodiment, an electrical stimulation system for providing therapy to a patient using intermittent electrical stimulation includes: an electrical stimulation lead with a lead body having a distal portion and a proximal portion; electrodes disposed along the distal portion of the lead; terminals disposed along the proximal portion of the lead; and lead conductors electrically coupling the electrodes to the terminals. A control module is coupleable to the lead. The control module includes: a housing; a processor disposed in the housing and coupled to the electrodes; and a rechargeable power source disposed in the housing and coupled to the processor. The power source is configured and arranged for storing energy and supplying the stored energy to the processor for stimulating patient tissue via the electrodes. The power source is configured and arranged to supply the processor with energy for no more than three hours of electrical stimulation before being depleted when fully charged.

In some embodiments, the power source does not comprise a battery. In some embodiments, the power source includes at least one capacitor.

In some embodiments, the power source is configured and arranged to supply the processor with energy for no more than two hours of electrical stimulation before being depleted when fully charged. In some embodiments, the power source is configured and arranged to supply the processor with energy for no more than one hour of electrical stimulation before being depleted when fully charged.

In some embodiments, the electrical stimulation system further includes a power-source recharger configured and arranged for recharging the implanted power source subsequent to depletion of the stored energy in the power source. In some embodiments, the power-source recharger is configured and arranged for remaining external to the patient during operation. In some embodiments, the power-source recharger is configured and arranged for recharging the implanted power source after a duration of time that is longer than a duration of time in which the energy stored in the power supply is depleted during electrical stimulation when fully charged. In some embodiments, the power-source recharger is configured and arranged for recharging the implanted power source for no more than fifteen minutes. In some embodiments, the power-source recharger is configured and arranged for recharging the implanted power source for no more than ten minutes.

In some embodiments, the electrical stimulation system further includes a connector for receiving the lead, the connector including a connector housing defining a port configured and arranged for receiving the proximal portion of the lead, and connector contacts disposed in the connector housing and configured and arranged to couple to the terminals of the lead when the proximal portion of the lead is received by the port. In some embodiments, the connector is disposed along the control module. In some embodiments, the electrical stimulation system includes a lead extension having a proximal portion and a distal portion, where the lead extension couples the lead to the control module. In some embodiments, the connector is disposed along the distal portion of the lead extension.

In some embodiments, the electrical stimulation system is configured and arranged for implanting into the patient for a period of time that is no less than one year.

In a further embodiment, a method for providing therapy to a patient using intermittent electrical stimulation includes: a) advancing a plurality of electrodes disposed along a distal portion of a lead to a target stimulation location within a patient; b) coupling a proximal portion of the lead to an electrical stimulator disposed external to the patient; c) stimulating patient tissue at the target stimulation location for a first duration of time that is no greater than twelve hours using the plurality of electrodes; d) ceasing stimulation after completion of the first duration of time; e) removing the lead from the patient after ceasing stimulation; and f) repeating steps a) through e) after completion of a second duration of time that is no less than three months from removing the lead from the patient.

In some embodiments, the second duration of time is at least five times longer than the first duration of time. In some embodiments, the second duration of time is at least ten times longer than the first duration of time.

In some embodiments, the method includes repeating steps a) through c) after completion of a third duration of time that is no less than one month from removing the lead from the patient. In some embodiments, the second duration of time is less than the third duration of time. In some embodiments, the second duration of time is greater than the third duration of time.

In some embodiments, the presence of the efficacious treatment is determined based, at least in part, on an observed reduction of patient pain as evaluated using a pain measurement scale. In some embodiments, the presence of the efficacious treatment is determined based, at least in part, on an observed frequency shift in the patient's theta wave activity.

In some embodiments, advancing a plurality of electrodes disposed along a distal portion of a lead to a target stimulation location within a patient includes advancing a plurality of electrodes disposed along a distal portion of a percutaneous lead to a target stimulation location within a patient.

In some embodiments, advancing a plurality of electrodes disposed along a distal portion of a lead to a target stimulation location within a patient includes advancing a plurality of electrodes to a target stimulation location within the epidural space of a patient.

In another embodiment, a method for providing therapy to a patient using intermittent electrical stimulation includes advancing a plurality of electrodes disposed along a distal portion of a lead to a target stimulation location within a patient. A proximal portion of the lead is coupled to an electrical stimulator disposed external to the patient. Patient tissue at the target stimulation location is stimulated for a first duration of time that is no greater than one day using the plurality of electrodes. The stimulation provides efficacious treatment to the patient for a second duration of time that is at least twice as long as the first duration of time. Stimulation is ceased after completion of the first duration of time. The lead is removed from the patient after ceasing stimulation and prior to an end of the second duration of time.

In some embodiments, the method includes implanting the electrical stimulation system into the patient prior to stimulating patient tissue.

In some embodiments, the power source does not comprise a battery. In some embodiments, the power source includes at least one capacitor.

In some embodiments, recharging the implanted power source subsequent to depletion of the stored energy in the power source includes recharging the implanted power source after a duration of time that is longer than a duration of time in which the energy stored in the power supply is depleted during electrical stimulation when fully charged.

In some embodiments, recharging the implanted power source subsequent to depletion of the stored energy in the power source includes recharging the implanted power source for no more than fifteen minutes. In some embodiments, recharging the implanted power source subsequent to depletion of the stored energy in the power source comprises recharging the implanted power source for no more than ten minutes.

In some embodiments, the power source is configured and arranged to supply the processor with energy for no more than two hours of electrical stimulation before being depleted when fully charged. In some embodiments, the power source is configured and arranged to supply the processor with energy for no more than one hour of electrical stimulation before being depleted when fully charged.

In some embodiments, implanting an electrical stimulation system into the patient comprises implanting an electrical stimulation system into the patient for a period of time that is no less than one year.

In yet another embodiment, a method for providing therapy to a patient using intermittent electrical stimulation includes stimulating patient tissue using an electrical stimulation system having a lead with a proximal portion and an opposing distal portion. Electrodes are disposed along the distal portion of the lead. A control module is coupled to a proximal portion of the lead. The control module includes a processor coupled to the plurality of electrodes, and a rechargeable power source coupled to the processor. The power source is configured and arranged for storing energy and supplying the stored energy to the processor for stimulating patient tissue via the plurality of electrodes. The power source is configured and arranged to supply the processor with energy for no more than three hours of electrical stimulation before being depleted when fully charged. The patient tissue is stimulated until the stored energy in the power source is depleted. The implanted power source is recharged subsequent to depletion of the stored energy in the power source using a power-source recharger that is external to the patient.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
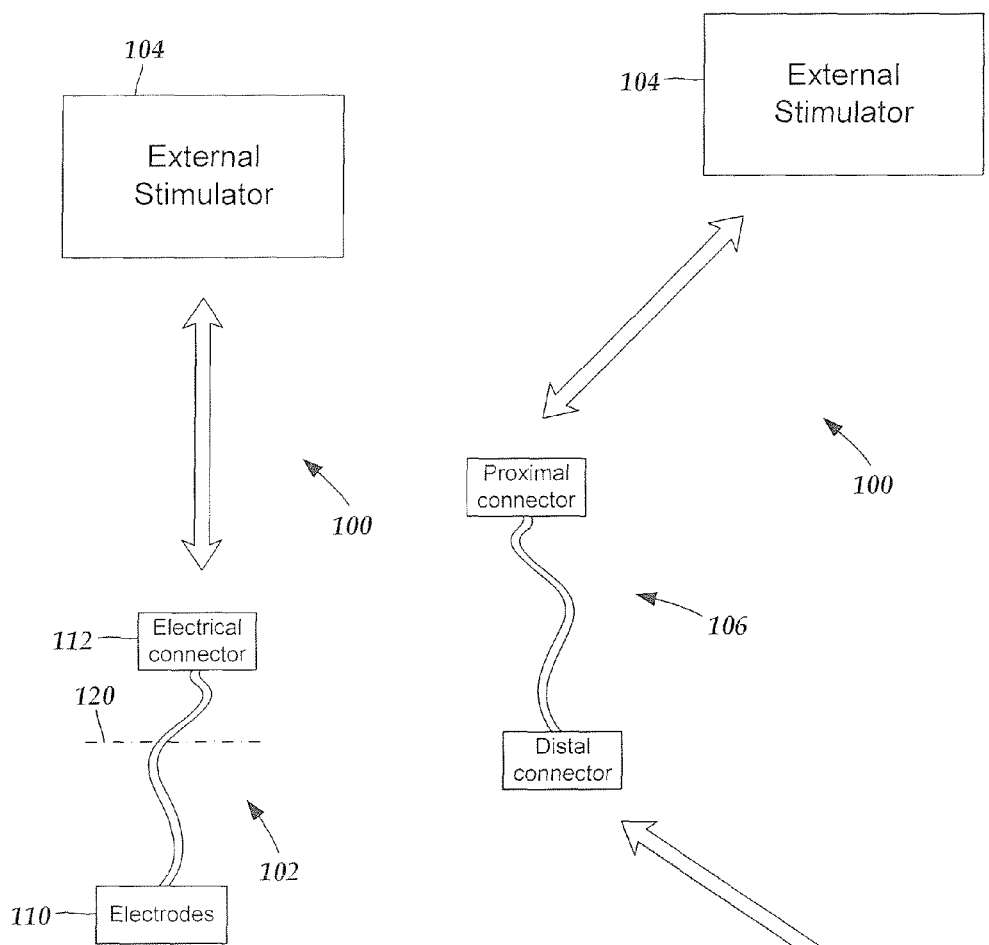
FIG. 1A is a schematic view of one embodiment of a trial stimulation system, according to the invention.
FIG. 1B is a schematic view of another embodiment of a trial stimulation system, according to the invention.

The present invention is directed to the area of electrical stimulation systems and methods of using the systems. The present invention is also directed to systems and methods for providing therapy to a patient using intermittent electrical stimulation generated from an electrical stimulation system.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181, 969; 6,516,227; 6,609,029; 6,609,032; 6,741,892; 7,244, 150; 7,450,997; 7,672,734; 7,761,165; 7,783,359; 7,792, 590; 7,809,446; 7,949,395; 7,974,706; 8,175,710; 8,224, 450; 8,271,094; 8,295,944; 8,364,278; and 8,391,985; U.S. Patent Applications Publication Nos. 2007/0150036; 2009/ 0187222; 2009/0276021; 2010/0076535; 2010/0268298; 2011/0004267; 2011/0078900; 2011/0130817; 2011/ 0130818; 2011/0238129; 2011/0313500; 2012/0016378; 2012/0046710; 2012/0071949; 2012/0165911; 2012/ 0197375; 2012/0203316; 2012/0203320; 2012/0203321; 2012/0316615; and 2013/0105071; and U.S. patent application Ser. Nos. 12/177,823 and 13/750,725, all of which are incorporated by reference.

It may be desirable to use an implantable electrical stimulation system to treat pain, or to manage disorders with symptoms or effects that may be reduced by electrical stimulation. For example, in the case of pain management, the electrical stimulation system may be used to create a paresthesia that provides relief to the patient by masking the pain. Electrical stimulation systems may also provide relief to the patient without creating a paresthesia.

The electrical stimulation system can be implanted into any suitable region of the body where the patient is experiencing pain (or other adverse effect) including, for example, the patient's epidural space, or in proximity to one or more dorsal root ganglia, dorsal horn, dorsal column, or some combination thereof. Examples of electrical stimulation systems suitable for stimulating dorsal root ganglia are found in, for example, U.S. Patent Applications Publication Nos. 2013/0317583; 2013/0317585; 2013/0317586; 2013/ 0317587; and 2013/0317588, all of which are incorporated by reference.

Providing therapy using electrical stimulation may be a long-term process. Consequently, many conventional stimulation systems provide stimulation (via one or more implanted leads) of the patient over an extended period of time, such as the lifetime of the system, the lifetime of the patient, or at least 1, 5, 10, 15, 20, or more years.

In some instances, long-term implantation of a conventional electrical stimulation system may not be desirable. For example, some patients may not tolerate long-term implantation of the electrical stimulation system, due to the size of the components of the system. In some instances, the pain experienced by the patient may not warrant implantation of a conventional electrical stimulation system. For example, the pain experienced by the patient may be sporadic, or may not be severe enough to warrant long-term implantation of a conventional electrical stimulation system.

In at least some instances, the patient may have a disorder where the patient receives long-term benefits from short-term stimulation. For example, the patient may have a disorder where the negative effects of the disorder are diminished, or even completely suppressed, by electrical stimulation for a period of time that exceeds, or even greatly exceeds, the amount of time for which the electrical stimulation is applied.

Turning to FIG. 1A, as herein described electrical stimulation techniques for providing therapy to a patient include use of an electrical stimulation system that provides stimulation to the patient in an intermittent manner. In some embodiments the patient receives therapy via intermittent stimulation by undergoing periodic short-term stimulation procedures using an electrical stimulation system using one or more leads that are temporarily inserted into the patient. The periodic short-term stimulation procedures each include partially inserting a lead (e.g., a percutaneous lead) of an electrical stimulation system into the patient, providing stimulation, then removing the lead.

The lead is typically inserted into the patient such that electrodes disposed along a distal portion of the lead are positioned in proximity to a target stimulation location (e.g., one or more particular spinal cord levels of the patient's epidural space) while a proximal portion of the lead remains external to the patient and is coupled to an external stimulator that provides stimulation current to the system. The lead may couple to the external stimulator via an electrical connector disposed along a proximal portion of the lead. The lead is typically long enough so that the electrical connector remains external to the patient during the stimulation procedure. Alternately, the lead may be entirely inserted into the patient and coupled to a lead extension that extends out of the patient.

In at least some embodiments, the lead is inserted into a patient using an epidural needle within which the lead is disposed. Once the lead is positioned, the epidural needle may be removed from the patient by sliding the epidural needle off the proximal end of the lead. In at least some cases, the lead is isodiametric to facilitate sliding of the epidural lead over the lead. After completion of the stimulation procedure, the lead is removed from the patient.

FIG. 1A illustrates, in schematic view, one embodiment of an electrical stimulation system 100 that includes a lead 102 that is configured and arranged to couple directly to an external stimulator 104. FIG. 1B illustrates, in schematic view, another embodiment of the electrical stimulation system 100 that includes the lead 102 and one or more cables 106 that couple to the lead 102 and that are configured and arranged to also couple to the external electrical stimulator 104. The lead 102 includes electrodes 110 and an electrical connector 112. During operation, the electrodes 110 are disposed within the patient, while the electrical connector 112 remains external to the patient, as shown in FIGS. 1A and 1B by a line 120 schematically representing patient skin.

As shown in FIGS. 1A and 1B, the electrical connector 112 is configured and arranged to couple to the external stimulator 104. In at least some embodiments, the electrical connector 112 is configured and arranged to couple directly to the external stimulator 104, as shown in FIG. 1A. In at least some embodiments, the electrical connector 112 is configured and arranged to couple to the external stimulator 104 via one or more cables 106 as shown in FIG. 1B.

During a stimulation procedure, the electrical stimulation system 100 is used to provide efficacious treatment to the patient. Stimulation may, in some embodiments, occur during an all-in-one stimulation procedure. In which case, the lead may be inserted into the patient, and then removed (after a brief stimulation period) as part of a single procedure. Optionally, the stimulation procedure may be broken into separate portions. In which case, the lead may be inserted into the patient in one procedure, the patient may then receive stimulation for a period of time in a hospital, clinic, out-patient location, home, or other like facility. When the stimulation is ended, the lead is removed during a subsequent procedure.

The duration of the stimulation can be any suitable short-term period of time (e.g. no more than a day, twelve hours, six hours, three hours, two hours, one hour, thirty minutes, or less) before removing the lead. It will be understood that when the lead is not inserted into the patient, the electrical stimulation system is not providing stimulation to the patient.

The time duration of the efficacious treatment provided to the patient by the stimulation procedure may exceed the time duration of the stimulation. In other words, the patient may continue to feel the beneficial effects of the electrical stimulation for a period of time subsequent to the cessation of stimulation and removal of the lead. In at least some embodiments, the time duration of the efficacious treatment provided to the patient by the stimulation procedure exceeds the time duration of the stimulation by a multiple of the time duration of stimulation. In at least some embodiments, the time duration of the efficacious treatment provided to the patient by the stimulation procedure is one-and-a quarter, one-and-a-half, two, three, four, five, six, seven, eight, nine, ten, twenty, thirty, forty, fifty, sixty, seventy, eighty, ninety, one hundred, two hundred, three hundred, four hundred, five hundred, six hundred, seven hundred, eight hundred, nine hundred, one thousand, or more times the time duration of the stimulation.

The time duration of the efficacy of treatment provided by the stimulation can be determined using any suitable technique including, for example, an observed reduction of patient pain of at least 10%, 20%, 30%, 40%, 50%, 60%, 70%, or more. The reduction of patient pain may be observed by any suitable technique including, for example, using a pain measurement scale, patient feedback, a change in one or more monitored pain indicators (e.g., a frequency shift in the patient's theta wave activity), or the like.

In at least some embodiments, the patient may undergo successive insertion and stimulation procedures in regular intervals of time. The regular intervals of time between successive stimulation procedures may be at least one month, two months, three months, four months, six months, nine months, a year, eighteen months, two years, or longer. In at least some embodiments, the patient may undergo successive insertion and stimulation procedures in irregular intervals of time. For example, the patient may undergo a stimulation procedure based, at least in part, on an observance of reoccurring patient pain by the patient, medical practitioner, technician, or the like.

Figure 8:
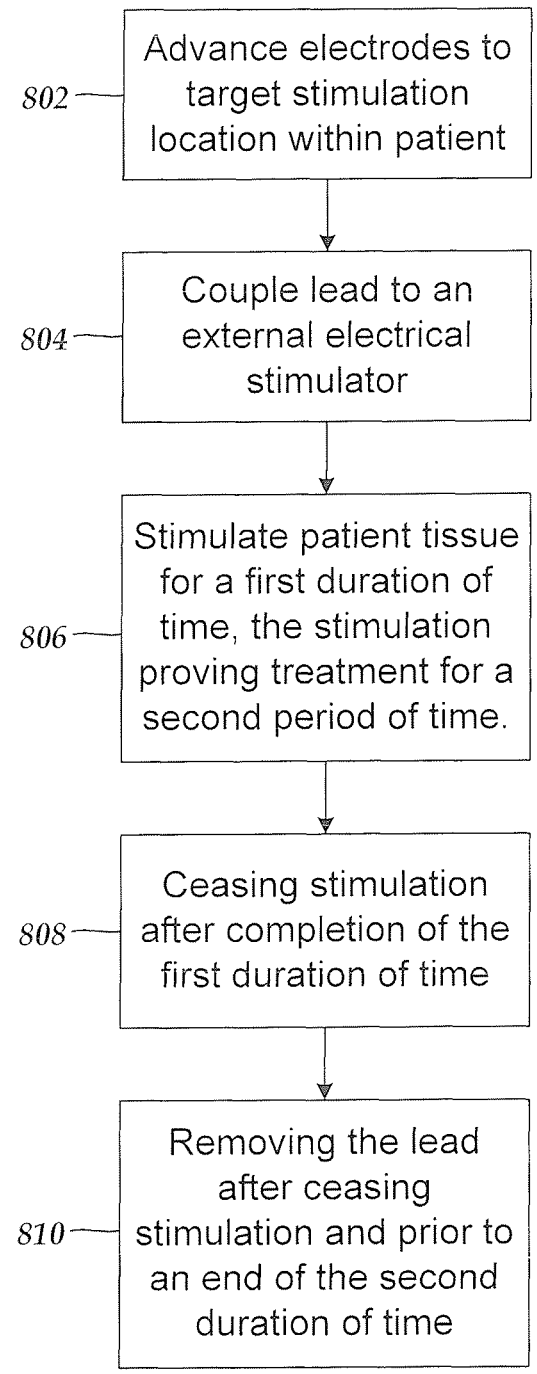
FIG. 8 is a flowchart of one embodiment of a stimulation procedure for providing therapy to a patient using intermittent electrical stimulation, according to the invention.

FIG. 8 is a flowchart showing one embodiment of a stimulation procedure for providing therapy to a patient using intermittent electrical stimulation. In step 802, electrodes disposed along a distal portion of a lead are advanced to a target stimulation location within a patient. In step 804, a proximal portion of the lead is coupled to an electrical stimulator disposed external to the patient. In step 806, patient tissue is stimulated at the target stimulation location for a first duration of time that is no greater than one day using the plurality of electrodes and that provides efficacious treatment to the patient for a second duration of time that is at least twice as long as the first duration of time. In step 808, stimulation is ceased after completion of the first duration of time. In step 810, the lead is removed from the patient after ceasing stimulation and prior to an end of the second duration of time.

Figure 2:
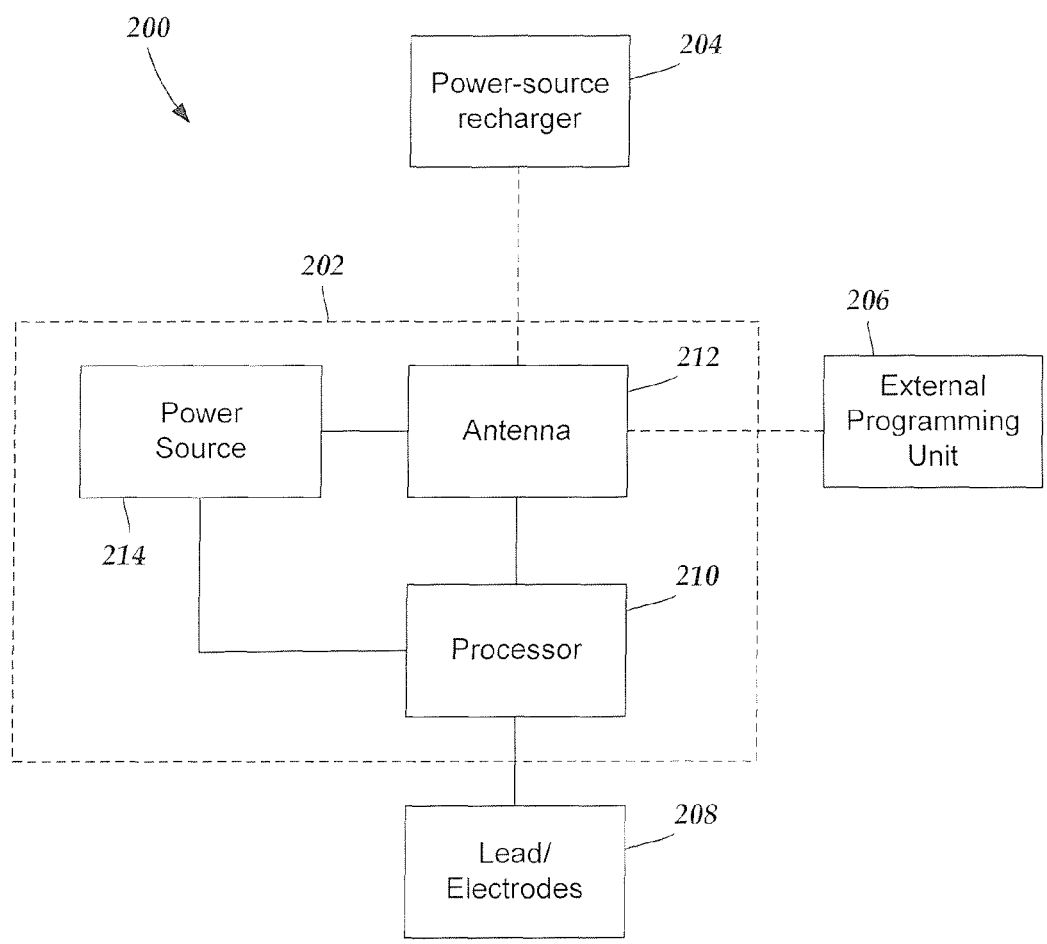
FIG. 2 is a schematic block diagram of one embodiment of an electrical stimulation system, according to the invention.

Turning to FIG. 2, in at least some embodiments the patient is electrically stimulated using an electrical stimulation system having an implantable control module that is smaller than conventional implantable control modules of electrical stimulation systems. In at least some embodiments, the electrical stimulation system includes an implantable, rechargeable power source that supplies enough energy to provide short-term stimulation to a patient, and that is suitable for being recharged using a power source that is external to the patient.

In many conventional electrical stimulation systems a lead is coupled to an implantable control module (e.g., an implantable pulse generator) that includes a power source that can be recharged and that is suitable for long-term (e.g., more than six months, one year, five years, or longer) use. The power source can be, for example, a battery. Such power sources, however, are relatively large when compared to other components of the implantable control module and necessitate implanting the control module away from the stimulation site in a portion of the body, such as the buttocks or large body cavity, where there is sufficient space for receiving the control module. The power source is often the largest element in the control module.

In contrast to conventional electrical stimulation systems, the electrical stimulation system described herein can include an implantable control module, lead, and power source suitable for long-term (e.g., more than six months, one year, five years, or longer) implantation that can be recharged and that is suitable for storing enough energy to enable "short-term" stimulation no more than 3 hours, 2 hours, 1 hour, 30 minutes, 20 minutes, 10 minutes, 5 minutes, or less) when fully charged. In some embodiments, the power source is suitable for storing enough energy to enable a longer stimulation (e.g., no more than two days, 36 hours, one day, 18 hours, 12 hours, 9 hours, 6 hours, or less). Enabling stimulation includes providing a trail of stimulation pulses having a frequency of at least 1 Hz with an amplitude and duration sufficient to stimulate patient tissue.

The electrical stimulation system can also include a power-source recharger that is external to the patient and that can be used to recharge the short-term power source. The power-source recharger transmits or otherwise delivers energy to the implanted control module or lead, via the power source, to provide stimulation current to patient tissue.

The duration of time needed to completely recharge the power source when fully depleted is typically less than the amount of time needed to entirely deplete the power source when fully charged. In at least some embodiments, the duration of time needed to completely recharge the power source when fully depleted is no more than 15 minutes, 10 minutes, 5 minutes, or less. It is advantageous to enable the power source to be completely charged in such a short amount of time. A "quick" recharge (e.g., in 15 minutes or less) makes it less onerous for the patient to recharge the power source than to recharge a conventional system. For example, a quick recharge can be performed while the patient engages in other activities, such as eating a meal, reading a magazine, watching television, sending emails, or engaging in a daily hygiene routine.

The power source can be recharged in regular or irregular intervals of time. In at least some embodiments, the power source is recharged subsequent to depletion of the stored energy in the power source. In at least some embodiments, the power source is recharged in regular intervals of time that are no less than twelve hours, eighteen hours, one day, two days, three days, four days, five days, six days, one week, or longer from the depletion of the stored energy from the previous charge. For example, the power source may be recharged as part of a daily routine. In at least some embodiments, the power source is recharged, as desired. For example, the power source may be recharged during a period of transient pain.

The power source can be disposed in the lead, the control module, partially in both the lead and the control module, or in neither as a stand-alone implantable component coupled to at least one of the lead or the control module. The stimulation system can include any suitable, small power source. In some embodiments, the power source is one or more capacitors, rechargeable batteries, or the like. In at least some embodiments, the power source is not a battery. In at least some embodiments, the power source is formed exclusively from one or more capacitors.

Using a power source that includes, for example, one or more capacitors may enable the power source to be smaller than power sources of conventional electrical stimulation systems. Thus, when the power source is disposed in the control module, the control module may be smaller than control modules of conventional electrical stimulation systems. The reduced-size of the power source (as compared to conventional power sources) may enable the control module to be implanted in a larger number of locations within the patient than a conventional control module. Additionally, the reduced-size of the power source (as compared to conventional power sources) may enable the control module, when implanted, to cause less discomfort to a patient than would the implantation of a control module with a conventional power source.

FIG. 2 illustrates schematically one embodiment of an electrical stimulation system 200 that includes an implantable control module (e.g., a stimulator or pulse generator) 202, one or more leads 208 with electrodes, an external power-source recharger 204, and an external programming unit 206. In at least some embodiments, the power-source recharger 204 and external programming unit 206 can be combined in a single device. In other embodiments, the power-source recharger 204 and external programming unit 206 can be separate devices.

Figure 3:
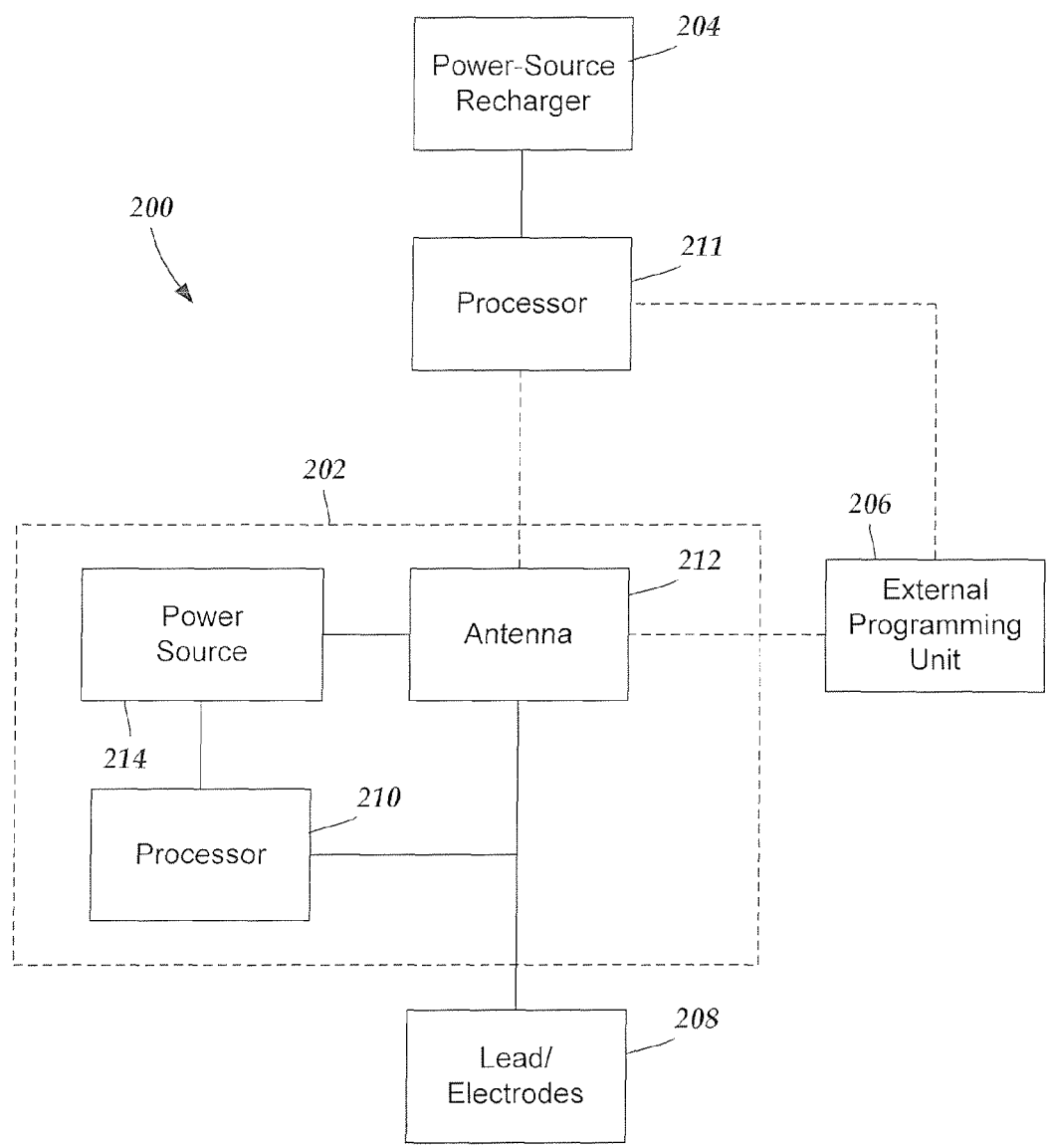
FIG. 3 is a schematic block diagram of another embodiment of an electrical stimulation system, according to the invention.

The lead 208 is coupled, or coupleable, to the implantable control module 202. The implantable control module 202 includes a power source 214, a processor 210, and an antenna 212. It will be understood that the electrical stimulation system can include more, fewer, or different components and can have a variety of different configurations including those configurations disclosed in the stimulator references cited herein. For example, FIG. 3 illustrates an alternative arrangement with an external processor 211, described below, that is coupled to the power-source recharger 204.

The power-source recharger 204 and the external programming unit 206 are not implanted within the patient. The power-source recharger 204 can be used to recharge the power source 214 through the antenna 212. The external programming unit 206 can be used to set or modify stimulation parameters stored by the processor 210 and used to determine the characteristics of the stimulation current provided to the tissue through the lead 208.

Any power-source recharger 204 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference.

The power-source recharger 204 can, itself, be rechargeable. In some embodiments, the power-source recharger 204 can be recharged wirelessly. In some embodiments, the power-source recharger 204 can be recharged by attachment to a wall socket or other recharging source. The patient may have two or more power-source rechargers so that he or she can exchange one power-source recharger for the other when, for example, the first is being recharged.

Any suitable, small power source can be used for the power source 214 including, but not limited to, one or more capacitors, rechargeable batteries, or the like. In at least some embodiments, the power source 214 is not a battery. The power source 214 typically has a relatively small amount of stored energy compared to the power-source recharger 204. In some embodiments, the power source 214 has a storage capacity of no more than 10%, 15%, or 25% of the storage capacity of the power-source recharger 204.

The power-source recharger 204 can be used to recharge the power source 214 after any suitable amount of time has elapsed. In some embodiments, the power-source recharger 204 can be used to recharge the power source 214 at some point after the power source 214 has used up all of its available energy. In which case, the patient undergoes a period of time between the power source 214 being drained of all of its energy supply and the power source being recharged. During this period of time, the electrical stimulation system is not providing stimulation to the patient. In some cases, the patient may continue to feel the beneficial effects of the electrical stimulation for a period of time subsequent to the cessation of stimulation.

Figure 4A:
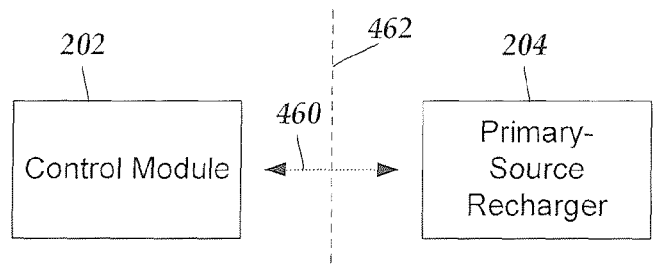
FIG. 4A is a schematic diagram of one embodiment of an arrangement of an external power-source recharger and a control module with wireless transmission, according to the invention.

Power is provided to the control module 202 (via the power source 214) by the power-source recharger 204 through wireless transmission (e.g., RF transmission or inductive coupling) via the antenna 212. FIG. 4A illustrates a wireless connection 460 across the skin boundary 462 between the control module 202 and the power-source recharger 204. The antenna 212 (see e.g., FIG. 3), or any other antenna described herein, can have any suitable configuration including, but not limited to, a coil, looped, or loopless configuration, or the like. In some embodiments, power is transmitted at a frequency of at least 50 kHz, 80 kHz, 100 kHz, or higher. In some embodiments, the power is transmitted at a frequency of at least 1 MHz, 5 MHz, or higher. In at least some embodiments, a higher transmission frequency will facilitate transmission over a longer distance. A transmission frequency may be selected based on government regulations, interference from other sources, or any combination of these and other factors.

The power-source recharger 204 and external programming unit 206 will typically also each include an antenna to transmit to, or receive transmission from, the control module 202. The antennas of the control module 202, power-source recharger 204 and external programming unit 206 may be designed for a particular transmission frequency or frequencies and there may be separate antennas, designed for different transmission frequencies, in the control module to communicate individually with the power-source recharger and the external programming unit.

Figure 4B:
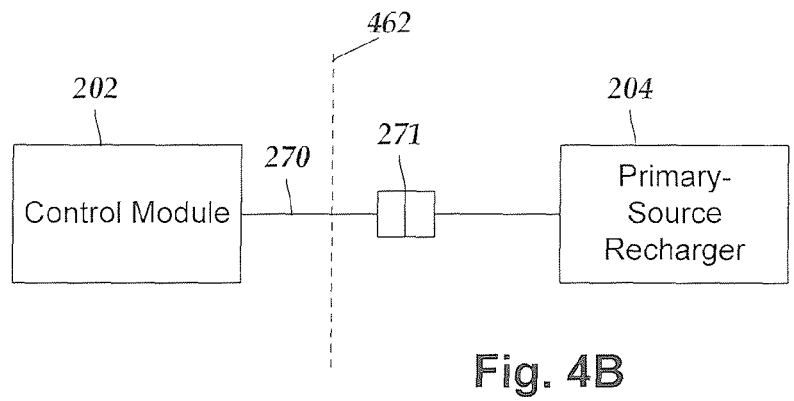
FIG. 4B is a schematic diagram of a second embodiment of an arrangement of an external power-source recharger and a control module with a wired connection, according to the invention.

As an alternative, the power-source recharger 204 can be coupled to the control module 202 by a cable 270 that extends into the patient, as illustrated in FIG. 4B. The cable may include an external connector 271 that allows the power-source recharger 204 to be uncoupled from the control module.

Figure 4C:
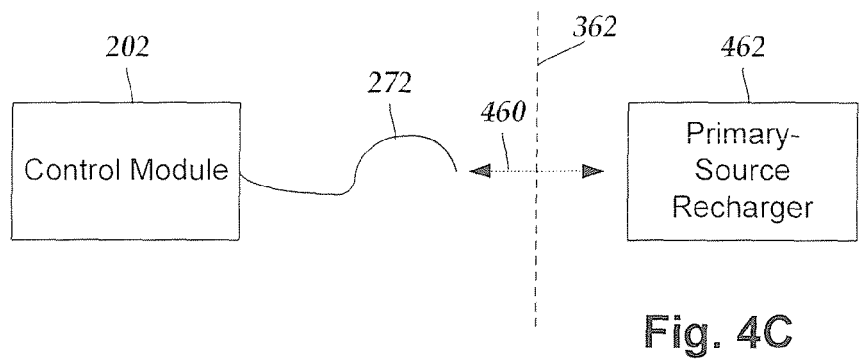
FIG. 4C is a schematic diagram of a third embodiment of an arrangement of an external power-source recharger and a control module with an antenna extending from the control module, according to the invention.

FIG. 4C illustrates another alternative in which an antenna 272 extends from a housing of the control module 202 and has a distal end positioned at a preselected placement position near the skin 462 for communication with the power-source recharger 204. It will be understood that the antenna 272, in this and any other embodiment described herein, may also incorporate any of the other elements of the control module 202 such as the processor 210 (or a portion of the processor) or the power source 214.

Figure 4D:
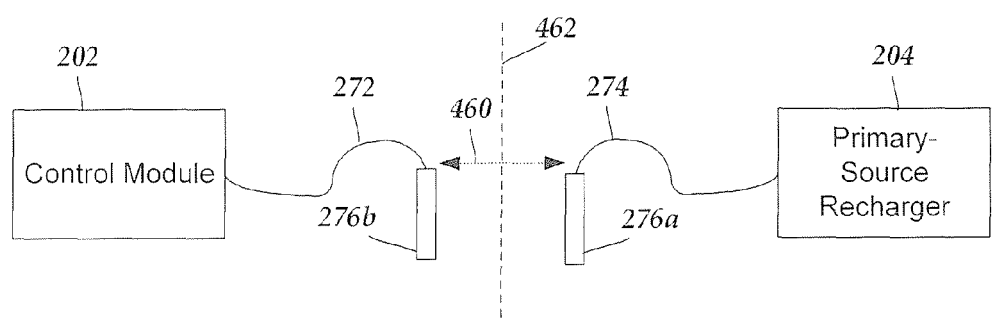
FIG. 4D is a schematic diagram of a fourth embodiment of an arrangement of an external power-source recharger and a control module with antennas extending from the control module and the power-source recharger, according to the invention.

FIG. 4D illustrates a further embodiment in which an internal antenna 272 extends from a housing of the control module 202 and has a distal end positioned at a preselected placement position near the skin 462 for communication with an external antenna 274 extending from the power-source recharger 204. In this embodiment, optional fixation elements 276a, 276b, such as magnets, may be provided so that the external antenna 274 can be attached to the skin 462 near the internal antenna 272.

Figure 4E:
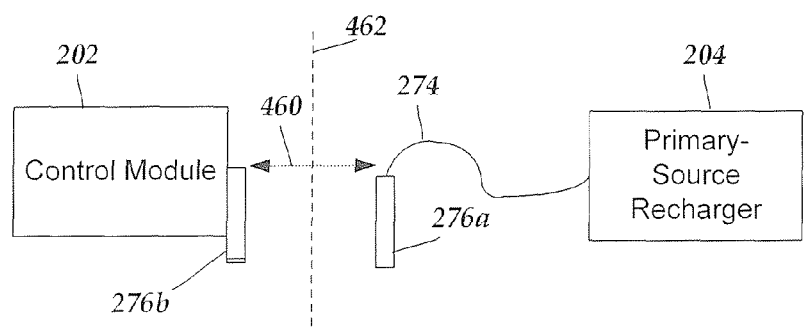
FIG. 4E is a schematic diagram of a fifth embodiment of an arrangement of an external power-source recharger and a control module with an antenna extending from the power-source recharger, according to the invention.

FIG. 4E illustrates yet another embodiment in which an antenna 274 extends from the power-source recharger 204 for communication with the control module 202. In this embodiment, optional fixation elements 276a. 276b, such as magnets, may be provided so that the antenna 274 can be attached to the skin 462 near the control module 202.

Returning to FIG. 2, in at least some embodiments, the processor 210 is configured to control one or more of the timing, frequency, strength, duration, and waveform of the pulses. In addition, the processor 210 can select which electrodes of the lead 208 can be used to provide stimulation, if desired. In some embodiments, the processor 210 selects which electrode(s) are cathodes and which electrode(s) are anodes. In some embodiments, the processor 210 is used to identify which electrodes provide the most useful stimulation of the desired tissue.

Any processor 210 can be used and can be as simple as an electronic device that, for example, produces pulses at a regular interval or the processor can be capable of receiving and interpreting instructions from the external programming unit 206 that, for example, allows modification of pulse characteristics. In the illustrated embodiment, the processor 210 is coupled to the antenna 212 to receive signals from the external programming unit 206.

Turning to FIG. 3, in alternative embodiments, the power-source recharger 204 includes a processor 211 that is similar to, or the same as, the processor 210 described above. The processor 211 can be used to generate the electrical stimulation current with desired stimulation parameters that are then delivered directly (or via the control module 202) to the lead 208. An optional second processor 210 can be included in the control module 202 to generate electrical stimulation current with desired stimulation parameters using the second power source 214. In some embodiments, both processors 210, 211 can be used to generate electrical stimulation current with desired stimulation parameters from the power-source recharger 204. The processor 211 and optional processor 210 can be programmed (for example, stimulation parameters set or modified) using the external programming unit 206. Alternatively or additionally, the processor 211 may be coupled to an input device that allows the stimulation parameters to be set or modified directly by a user without the external programming unit.

Returning to FIG. 2, the external programming unit 206 can be any unit that can provide information to the processor 210 or processor 211 via an antenna. One example of a suitable programming unit is a computer operated by the user or clinician to send signals to the control module 202. The signals sent to the processor 210 (or processor 211) via the antenna 212 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 200 to cease operation, to start operation, to start charging the power source 214, or to stop charging the power source. In some embodiments, the power-source recharger 204 and the external programming unit 206 can form a single device.

Optionally, the electrical stimulation system 200 may include a transmitter (not shown) coupled to the processor 210 and the antenna 212 for transmitting signals back to the external programming unit or another unit capable of receiving the signals. For example, the electrical stimulation system 200 may transmit signals indicating whether the electrical stimulation system 200 is operating properly or not or indicating when the power source needs to be charged or the level of charge remaining in the power source. The control unit 202 may also be capable of transmitting information about the pulse characteristics so that a user or clinician can determine or verify the characteristics.

Figure 5:
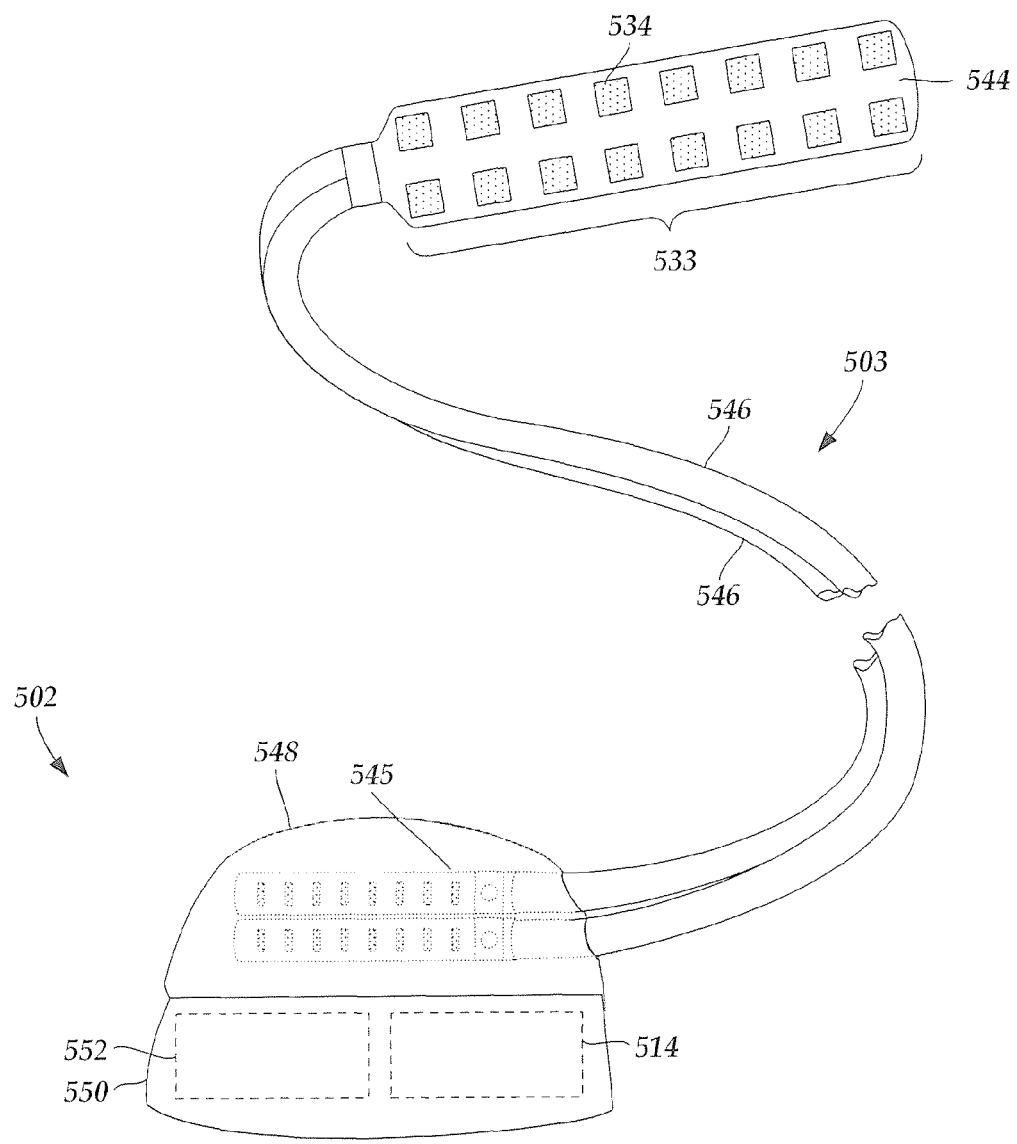
FIG. 5 is a schematic side view of one embodiment of an electrical stimulation system that includes a paddle lead electrically coupled to an implantable control module, according to the invention.

FIG. 5 illustrates one embodiment of a control module 502 and a lead 503. The lead 503 includes a paddle body 544 and one or more lead bodies 546. In FIG. 5, the lead 503 is shown having two lead bodies 546. It will be understood that the lead 503 can include any suitable number of lead bodies including, for example, one, two, three, four, five, six, seven, eight or more lead bodies 546. An array of electrodes 533, such as electrode 534, is disposed on the paddle body 544, and one or more terminals (e.g., 760 in FIGS. 7A-7B) are disposed along each of the one or more lead bodies 546. In at least some embodiments, the lead has more electrodes than terminals.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 6:
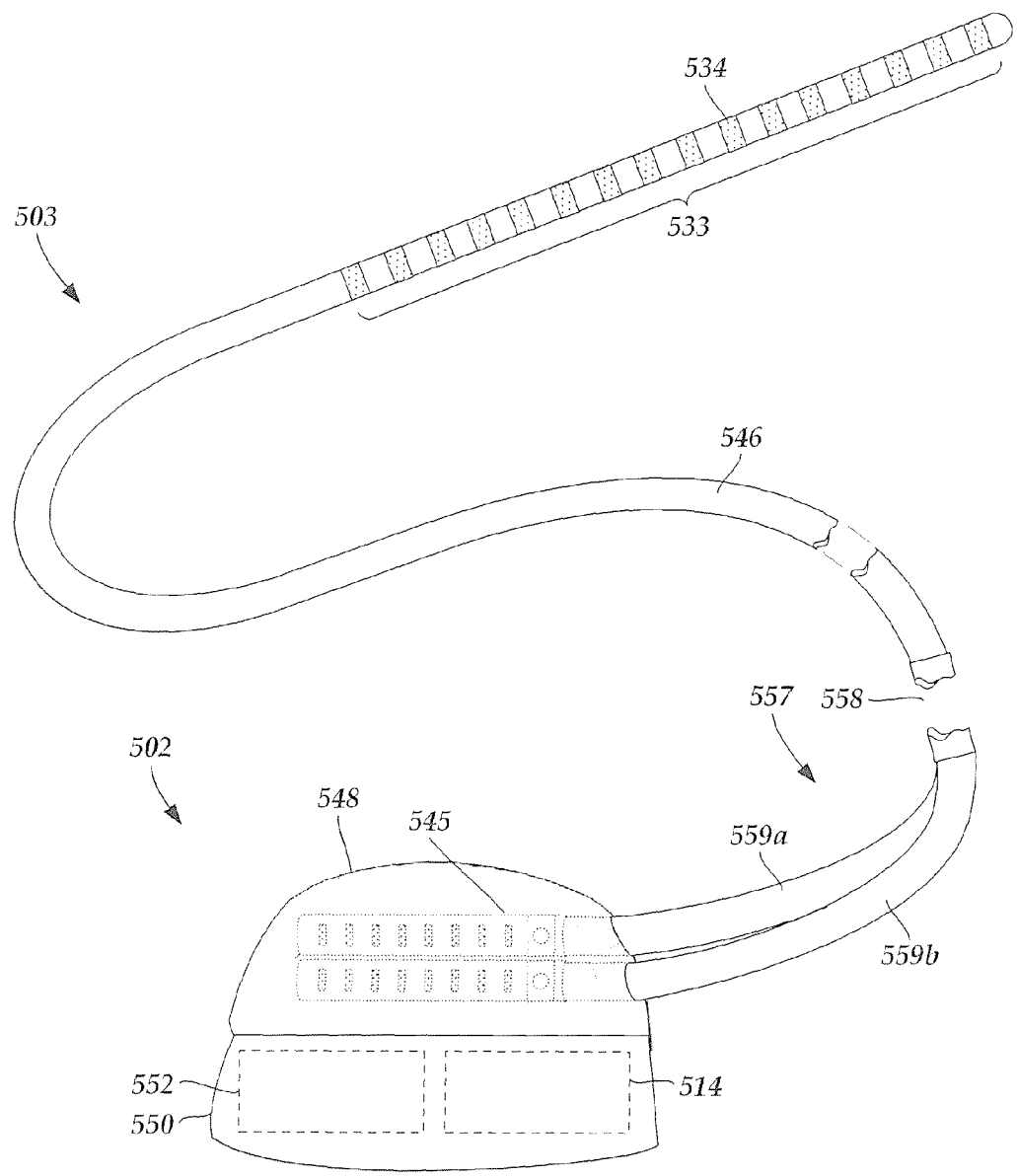
FIG. 6 is a schematic side view of one embodiment of an electrical stimulation system that includes a percutaneous lead electrically coupled to an implantable control module, according to the invention.

FIG. 6 illustrates schematically another embodiment in which the lead 503 is a percutaneous lead. In FIG. 6, the electrodes 534 are shown disposed along the one or more lead bodies 546. In at least some embodiments, the lead 503 is isodiametric along a longitudinal length of the lead body 546.

The lead 503 can be coupled to the implantable control module 502 in any suitable manner. In FIG. 5, the lead 503 is shown coupling directly to the implantable control module 502. In at least some other embodiments, the lead 503 couples to the implantable control module 502 via one or more intermediate devices (700 in FIGS. 7A-7B). For example, in at least some embodiments one or more lead extensions 724 (see e.g., FIG. 7B) can be disposed between the lead 503 and the implantable control module 502 to extend the distance between the lead 503 and the implantable control module 502. Other intermediate devices may be used in addition to, or in lieu of, one or more lead extensions including, for example, a splitter, an adaptor, or the like or combinations thereof. It will be understood that, in the case where the electrical stimulation system includes multiple elongated devices disposed between the lead 503 and the implantable control module 502, the intermediate devices may be configured into any suitable arrangement.

In FIG. 6, the electrical stimulation system 500 is shown having a splitter 557 configured and arranged for facilitating coupling of the lead 503 to the implantable control module 502. The splitter 557 includes a splitter connector 558 configured to couple to a proximal end of the lead 503, and one or more splitter tails 559a and 559b configured and arranged to couple to the implantable control module 502 (or another splitter, a lead extension, an adaptor, or the like).

The implantable control module 502 includes a connector housing 548 and a sealed electronics housing 550. An electronic subassembly 552 (which includes the processor 210 (see, FIG. 2) and the power source 514 are disposed in the electronics housing 550. A connector 545 is disposed in the connector housing 548. The connector 545 is configured and arranged to make an electrical connection between the lead 503 and the electronic subassembly 552 of the implantable control module 502.

The electrical stimulation system or components of the electrical stimulation system, including the paddle body 544, the one or more of the lead bodies 546, and the implantable control module 502, are typically implanted into the body of a patient. The electrical stimulation system can be used for a variety of applications including, but not limited to deep brain stimulation, neural stimulation, spinal cord stimulation, muscle stimulation, and the like.

The electrodes 534 can be formed using any conductive, biocompatible material. Examples of suitable materials include metals, alloys, conductive polymers, conductive carbon, and the like, as well as combinations thereof. In at least some embodiments, one or more of the electrodes 534 are formed from one or more of: platinum, platinum iridium, or titanium.

Any suitable number of electrodes 534 can be disposed on the lead including, for example, four, five, six, seven, eight, nine, ten, eleven, twelve, fourteen, sixteen, twenty-four, thirty-two, or more electrodes 534. In the case of paddle leads, the electrodes 534 can be disposed on the paddle body 544 in any suitable arrangement. In FIG. 5, the electrodes 534 are arranged into two columns, where each column has eight electrodes 534.

The electrodes of the paddle body 544 (or one or more lead bodies 546) are typically disposed in, or separated by, a non-conductive, biocompatible material such as, for example, silicone, polyurethane, polyetheretherketone ("PEEK"), epoxy, and the like or combinations thereof. The one or more lead bodies 546 and, if applicable, the paddle body 544 may be formed in the desired shape by any process including, for example, molding (including injection molding), casting, and the like. The non-conductive material typically extends from the distal ends of the one or more lead bodies 546 to the proximal end of each of the one or more lead bodies 546.

In the case of paddle leads, the non-conductive material typically extends from the paddle body 544 to the proximal end of each of the one or more lead bodies 546. Additionally, the non-conductive, biocompatible material of the paddle body 544 and the one or more lead bodies 546 may be the same or different. Moreover, the paddle body 544 and the one or more lead bodies 546 may be a unitary structure or can be formed as two separate structures that are permanently or detachably coupled together.

Figure 7A:
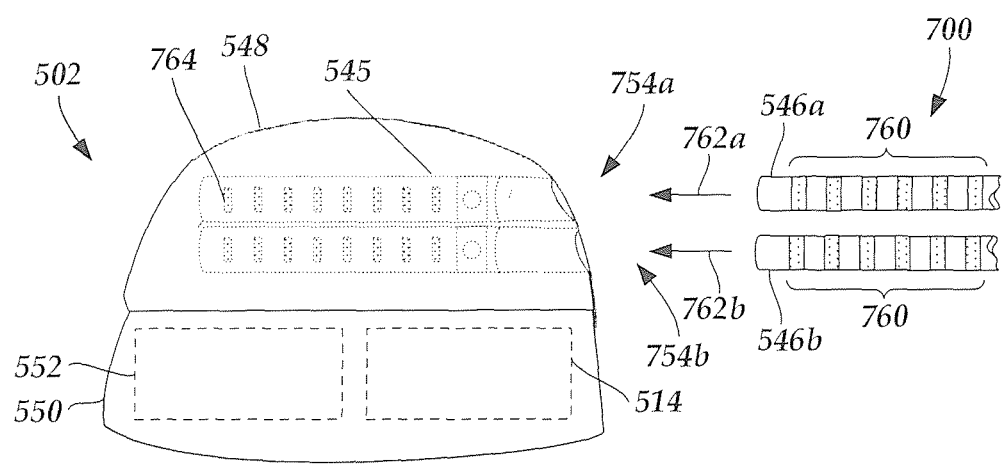
FIG. 7A is a schematic side view of one embodiment of the implantable control module of FIG. 5 configured and arranged to electrically couple to an elongated device, according to the invention.
Figure 7B:
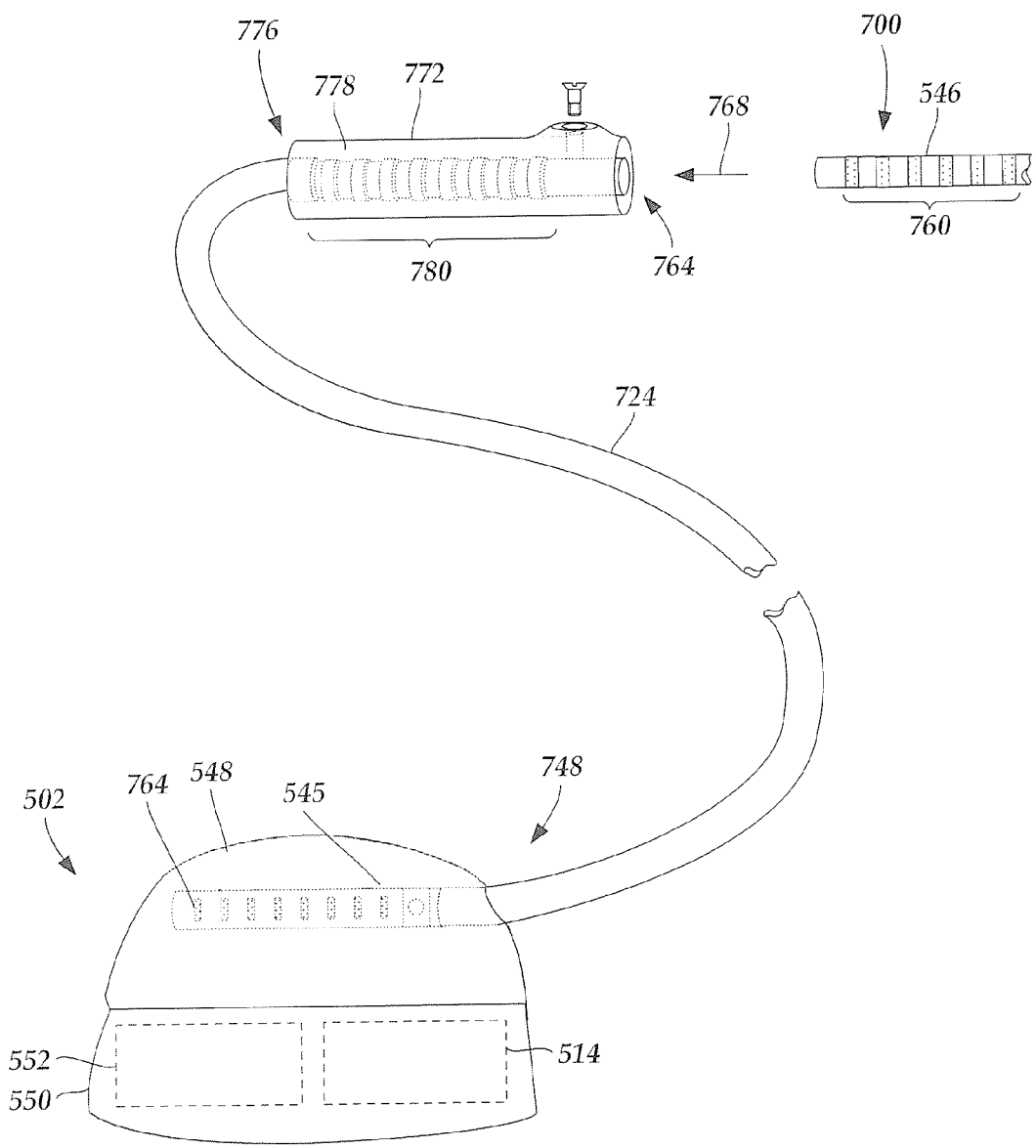
FIG. 7B is a schematic side view of one embodiment of a lead extension configured and arranged to electrically couple the elongated device to the implantable control module of FIG. 5, according to the invention.

One or more terminals (e.g., 760 in FIGS. 7A-7B) are typically disposed along the proximal end of the one or more lead bodies 546 of the electrical stimulation system 500 (as well as any splitters, lead extensions, adaptors, or the like) for electrical connection to corresponding connector contacts (e.g., 764 in FIGS. 7A-7B). The connector contacts are disposed in connectors (e.g., 545 in FIGS. 5-7B; and 772 FIG. 7B) which, in turn, are disposed on, for example, the implantable control module 502 (or a lead extension, a splitter, an adaptor, or the like). One or more electrically conductive wires, cables, or the like (i.e., "conductors"—not shown) extend from the terminal(s) to the electrode(s). In at least some embodiments, there is at least one (or exactly one) terminal conductor for each terminal which extends to at least one (or exactly one) of the electrodes.

The one or more conductors are embedded in the non-conductive material of the lead body 546 or can be disposed in one or more lumens (not shown) extending along the lead body 546. For example, any of the conductors may extend distally along the lead body 546 from the terminals 760.

FIG. 7A is a schematic side view of one embodiment of a proximal end of one or more elongated devices 700 configured and arranged for coupling to one embodiment of the connector 545. The one or more elongated devices may include, for example, one or more of the lead bodies 546 of FIG. 5, one or more intermediate devices (e.g., a splitter, the lead extension 724 of FIG. 7B, an adaptor, or the like or combinations thereof), or a combination thereof.

The connector 545 defines at least one port into which a proximal ends 546a, 546b of the elongated device 700 can be inserted, as shown by directional arrows 762a, 762b. In FIG. 7A (and in other figures), the connector housing 548 is shown having two ports 754a, 754b. The connector housing 548 can define any suitable number of ports including, for example, one, two, three, four, five, six, seven, eight, or more ports.

The connector 545 also includes one or more connector contacts, such as connector contact 764, disposed within each port 754a, 754b. When the elongated device 700 is inserted into the ports 754a, 754b, the connector contact(s) 764 can be aligned with the terminal(s) 760 disposed along the proximal end(s) of the elongated device(s) 700 to electrically couple the implantable control module 502 to the electrodes (534 of FIG. 5) disposed on the paddle body 545 of the lead 503. Examples of connectors in implantable control modules are found in, for example, U.S. Pat. Nos. 7,244,150 and 8,224,450, which are incorporated by reference.

FIG. 7B is a schematic side view of another embodiment of the electrical stimulation system 500. The electrical stimulation system 500 includes a lead extension 724 that is configured and arranged to couple one or more elongated devices 700 (e.g., one of the lead bodies 546 of FIGS. 5 and 6, the splitter 557 of FIG. 6, an adaptor, another lead extension, or the like or combinations thereof) to the implantable control module 502. In FIG. 7B, the lead extension 624 is shown coupled to a single port 754 defined in the connector 545. Additionally, the lead extension 724 is shown configured and arranged to couple to a single elongated device 700. In alternate embodiments, the lead extension 724 is configured and arranged to couple to multiple ports 754 defined in the connector 545, or to receive multiple elongated devices 700, or both.

A lead extension connector 772 is disposed on the lead extension 724. In FIG. 7B, the lead extension connector 772 is shown disposed at a distal end 776 of the lead extension 724. The lead extension connector 772 includes a connector housing 778. The connector housing 778 defines at least one port 764 into which terminal(s) 760 of the elongated device 700 can be inserted, as shown by directional arrow 738. The connector housing 778 also includes a plurality of connector contacts, such as connector contact 780. When the elongated device 700 is inserted into the port 730, the connector contacts 780 disposed in the connector housing 778 can be aligned with the terminal(s) 760 of the elongated device 700 to electrically couple the lead extension 724 to the electrodes (534 of FIGS. 5 and 6) disposed along the lead (503 in FIGS. 5 and 6).

In at least some embodiments, the proximal end of the lead extension 724 is similarly configured and arranged as a proximal end of the lead 503 (or other elongated device 700). The lead extension 724 may include one or more electrically conductive wires (not shown) that electrically couple the connector contact(s) 780 to a proximal end 748 of the lead extension 724 that is opposite to the distal end 776. The conductive wire(s) disposed in the lead extension 724 can be electrically coupled to one or more terminals (not shown) disposed along the proximal end 748 of the lead extension 724. The proximal end 748 of the lead extension 724 is configured and arranged for insertion into a connector disposed in another lead extension (or another intermediate device). As shown in FIG. 7B, the proximal end 748 of the lead extension 724 is configured and arranged for insertion into the connector 545.

The embodiments of FIGS. 5-7B illustrate a control module 502 with a connector 5F45 into which a proximal end portion of the lead or lead extension can be removably inserted. It will be recognized, however, that other embodiments of a control module and lead can have the lead or lead extension permanently attached to the control module. Such an arrangement can reduce the size of the control module as the conductors in the lead can be permanently attached to the electronic subassembly. It will also be recognized that, in at least some embodiments, more than one lead can be attached to a control module.

Figure 9:
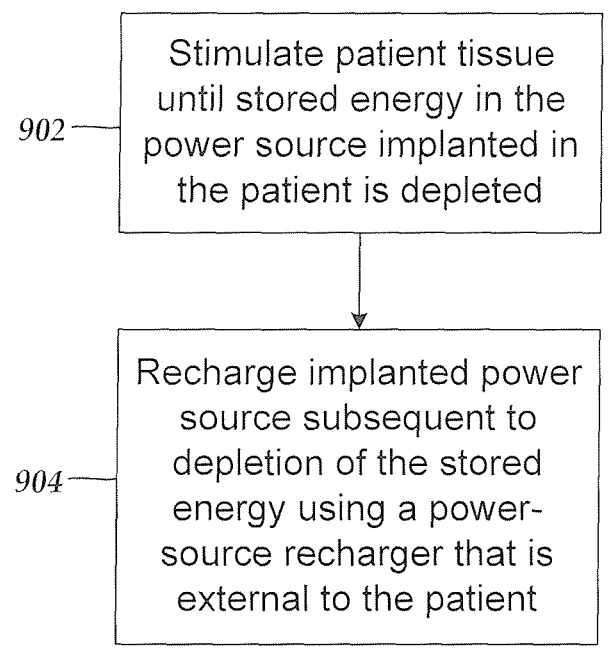
FIG. 9 is a flowchart of another embodiment of a stimulation procedure for providing therapy to a patient using intermittent electrical stimulation, according to the invention.

FIG. 9 is a flowchart showing another embodiment of a stimulation procedure for providing therapy to a patient using intermittent electrical stimulation. In step 902, patient tissue is stimulated using an electrical stimulation system. The stimulation system may, optionally, include a lead having a proximal portion and an opposing distal portion, electrodes disposed along the distal portion of the lead, and a control module coupled to a proximal portion of the lead. The control module may include a processor coupled to the electrodes, and a rechargeable power source coupled to the processor. The power source can be configured and arranged for storing energy and supplying the stored energy to the processor for stimulating patient tissue via the electrodes. The power source may be configured and arranged to supply the processor with energy for no more than some period of time (e.g., three hours) of electrical stimulation before being depleted when fully charged. The patient tissue may be stimulated until the stored energy in the power source is depleted. In step 904, the implanted power source is recharged subsequent to depletion of the stored energy in the power source using a power-source recharger that is external to the patient.

It will be understood that the system can include one or more of the methods described hereinabove with respect to FIGS. 8 and 9 in any combination. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks or described for the control modules, external programming units, remote data storage units, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A method for providing therapy to a patient using intermittent electrical stimulation, the method comprising:
   a) advancing a plurality of electrodes disposed along a distal portion of a lead to a target stimulation location within a patient;
   b) coupling a proximal portion of the lead to an electrical stimulator disposed external to the patient;
   c) stimulating patient tissue at the target stimulation location for a first duration of time that is no greater than one day using the plurality of electrodes, the stimulation providing efficacious treatment to the patient for a second duration of time that is at least twice as long as the first duration of time, wherein the presence of the efficacious treatment is determined based, at least in part, on an observed reduction of patient pain as evaluated using a pain measurement scale;

d) ceasing stimulation after completion of the first duration of time; and
e) removing the lead from the patient after ceasing stimulation and prior to an end of the second duration of time.

2. The method of claim 1, wherein the second duration of time is at least five times longer than the first duration of time.

3. The method of claim 1, wherein the second duration of time is at least ten times longer than the first duration of time.

4. The method of claim 1, further comprising repeating steps a) through e) after completion of a third duration of time that is no less than one month from removing the lead from the patient.

5. The method of claim 4, wherein the second duration of time is less than the third duration of time.

6. The method of claim 4, wherein the second duration of time is greater than the third duration of time.

7. A method for providing therapy to a patient using intermittent electrical stimulation, the method comprising:
a) advancing a plurality of electrodes disposed along a distal portion of a lead to a target stimulation location within a patient;
b) coupling a proximal portion of the lead to an electrical stimulator disposed external to the patient;
c) stimulating patient tissue at the target stimulation location for a first duration of time that is no greater than one day using the plurality of electrodes, the stimulation providing efficacious treatment to the patient for a second duration of time that is at least twice as long as the first duration of time, wherein the presence of the efficacious treatment is determined based, at least in part, on an observed frequency shift in the patient's theta wave activity;
d) ceasing stimulation after completion of the first duration of time; and
e) removing the lead from the patient after ceasing stimulation and prior to an end of the second duration of time.

8. The method of claim 1, wherein advancing a plurality of electrodes disposed along a distal portion of a lead to a target stimulation location within a patient comprises advancing a plurality of electrodes disposed along a distal portion of a percutaneous lead to a target stimulation location within a patient.

9. The method of claim 1, wherein advancing a plurality of electrodes disposed along a distal portion of a lead to a target stimulation location within a patient comprises advancing a plurality of electrodes to a target stimulation location within an epidural space of a patient.

10. A method for providing therapy to a patient using intermittent electrical stimulation, the method comprising:
stimulating patient tissue using an electrical stimulation system comprising a lead having a proximal portion and an opposing distal portion, a plurality of electrodes disposed along the distal portion of the lead, and an implantable control module coupled to the proximal portion of the lead, the control module comprising a processor coupled to the plurality of electrodes, and a rechargeable power source coupled to the processor, the power source configured and arranged for storing energy and supplying the stored energy to the processor for stimulating patient tissue via the plurality of electrodes, wherein the power source is configured and arranged to supply the processor with energy for no more than three hours of electrical stimulation before being depleted when fully charged, wherein the patient tissue is stimulated until the stored energy in the power source is depleted; and
recharging the implanted power source subsequent to depletion of the stored energy in the power source using a power-source recharger that is external to the patient.

11. The method of claim 10, further comprising implanting the electrical stimulation system into the patient prior to stimulating patient tissue.

12. The method of claim 10, wherein the power source does not comprise a battery.

13. The method of claim 10, wherein the power source comprises at least one capacitor.

14. The method of claim 10, wherein recharging the implanted power source subsequent to depletion of the stored energy in the power source comprises recharging the implanted power source after a duration of time that is longer than a duration of time in which the energy stored in the power supply is depleted during electrical stimulation when fully charged.

15. The method of claim 10, wherein recharging the implanted power source subsequent to depletion of the stored energy in the power source comprises recharging the implanted power source for no more than fifteen minutes.

16. The method of claim 10, wherein recharging the implanted power source subsequent to depletion of the stored energy in the power source comprises recharging the implanted power source for no more than ten minutes.

17. The method of claim 10, wherein the power source is configured and arranged to supply the processor with energy for no more than two hours of electrical stimulation before being depleted when fully charged.

18. The method of claim 10, wherein the power source is configured and arranged to supply the processor with energy for no more than one hour of electrical stimulation before being depleted when fully charged.

19. The method of claim 10, wherein implanting an electrical stimulation system into the patient comprises implanting an electrical stimulation system into the patient for a period of time that is no less than one year.

* * * * *